US006751287B1

(12) United States Patent
Kalyon et al.

(10) Patent No.: US 6,751,287 B1
(45) Date of Patent: Jun. 15, 2004

(54) METHOD AND APPARATUS FOR X-RAY ANALYSIS OF PARTICLE SIZE (XAPS)

(75) Inventors: Dilhan M. Kalyon, Teaneck, NJ (US); Rahmi Yazici, deceased, late of Union City, NJ (US), by Dostum F. Yazici, legal representative

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 0 days.

(21) Appl. No.: 09/700,350

(22) PCT Filed: May 14, 1999

(86) PCT No.: PCT/US99/10723

§ 371 (c)(1),
(2), (4) Date: Feb. 5, 2002

(87) PCT Pub. No.: WO99/60388

PCT Pub. Date: Nov. 25, 1999

Related U.S. Application Data

(60) Provisional application No. 60/085,548, filed on May 15, 1998.

(51) Int. Cl.⁷ .............................................. G01N 23/20
(52) U.S. Cl. .............................. 378/71; 378/72; 378/73; 378/75
(58) Field of Search .......................... 378/70, 71, 72, 378/73, 75, 79, 81, 82, 84

(56) References Cited

U.S. PATENT DOCUMENTS

| | | | |
|---|---|---|---|
| 2,428,796 A | 10/1947 | Friedman ..................... | 378/71 |
| 2,805,342 A | 9/1957 | Lang ........................... | 378/71 |
| 2,805,343 A | 9/1957 | Lang ........................... | 378/71 |
| 2,843,749 A | 7/1958 | Koblenz ....................... | 378/49 |
| 3,148,275 A | 9/1964 | Mack .......................... | 378/75 |
| 3,440,419 A | 4/1969 | Das Gupta et al. ........... | 378/46 |
| 3,666,943 A * | 5/1972 | Carr-Brion et al. ........... | 378/44 |
| 3,702,933 A | 11/1972 | Fields et al. .................. | 378/70 |
| 3,749,910 A * | 7/1973 | Carr-Brion et al. ........... | 378/86 |
| 3,792,252 A | 2/1974 | Afanasiev et al. ............ | 378/70 |
| 4,144,450 A | 3/1979 | Goebel ........................ | 378/75 |
| 4,199,678 A | 4/1980 | Ladell ......................... | 378/75 |
| 4,592,082 A | 5/1986 | Pawloski ..................... | 378/75 |
| 4,641,329 A | 2/1987 | Green et al. .................. | 378/79 |
| 4,642,811 A | 2/1987 | Georgopoulos .............. | 378/53 |
| 4,649,556 A | 3/1987 | Rinik et al. ................... | 378/71 |

(List continued on next page.)

OTHER PUBLICATIONS

B. D. Cullity. Elements of X–Ray Diffraction, 2nd Edition (Reading, MA: Addision–Wesley, 1978), p. 126–131, 277–278, 281–285.*

Yazici, et al., "Defect Structure Analysis of Polycrystalline Materials by Computer–Controlled Double–Crystal Diffractometer with Position–Sensitive Detector," J. Appl. Cryst. (1983) 16, 89–95.

Primary Examiner—David V. Bruce
Assistant Examiner—Allen C. Ho
(74) Attorney, Agent, or Firm—Wolff & Samson PC

(57) ABSTRACT

The apparatus comprises an X-ray source (112), a monochromator (118), a goniometer (170), a position sensitive detector (150), a mechanism to rock or rotate the sample or the X-ray source and computer means (160) for interpreting the data obtained at the position sensitive detector. The method of the present invention includes the steps of generating an X-ray; narrowing the wavelength of the X-ray beam; allowing the particles to diffract the beam; detecting the diffracted beam with a position sensitive detector, collecting the diffraction data from individual particles; rocking or rotating the specimen or the X-ray source for successive times to cover the angular range of reflection of the particles; compilation of the diffraction data in the computer memory to construct the intensity profile for the individual particles; and interpreting the data to determine particle size and particle size distribution.

26 Claims, 15 Drawing Sheets

U.S. PATENT DOCUMENTS

| | | | |
|---|---|---|---|
| 4,821,301 A | 4/1989 | Cocks et al. | 378/70 |
| 4,918,712 A | 4/1990 | Le Floc'h et al. | 378/89 |
| 5,003,569 A | 3/1991 | Okada et al. | 378/70 |
| 5,128,976 A | 7/1992 | Moulai | 378/81 |
| 5,249,216 A * | 9/1993 | Ohsugi et al. | 378/46 |
| 5,373,544 A | 12/1994 | Goebel | 378/71 |
| 5,414,747 A * | 5/1995 | Ruud et al. | 378/73 |
| 5,418,828 A | 5/1995 | Carpenter | 378/71 |
| 5,446,777 A | 8/1995 | Houtman | 378/45 |
| 5,748,509 A | 5/1998 | Fewster | 364/578 |
| 5,784,432 A * | 7/1998 | Kurtz et al. | 378/70 |
| 5,878,106 A * | 3/1999 | Fujiwara | 378/79 |
| 6,285,736 B1 * | 9/2001 | Dosho | 378/79 |
| 6,301,330 B1 * | 10/2001 | Kurtz et al. | 378/71 |
| 6,459,763 B1 * | 10/2002 | Koinuma et al. | 378/71 |

* cited by examiner

METHOD AND APPARATUS FOR X-RAY ANALYSIS OF PARTICLE SIZE (XAPS)

This application is a U.S. National Phase Application under 35 U.S.C. § 371 of PCT Application Ser. No. PCT/US99/10723 filed May 14, 1999, which claims the benefit of U.S. Provisional Application Ser. No. 60/085,548 filed May 15, 1998. The entire disclosures each of these applications is expressly incorporated herein by reference.

BACKGROUND OF THE INVENTION

1. Field of the Invention

The present invention generally relates to a method and apparatus for x-ray analysis of particle size, XAPS for short, and more specifically to a method and apparatus for determining particle size and particle size distribution of crystalline particles comprising powders, suspensions or solids non-intrusively without the need to extractor separate the particles from the other ingredients of the materials.

2. Related Art

The overwhelming majority of materials handled by industry, such as mining, chemicals, construction, agriculture and waste products, are in particle or "powder" form. Many technologically important materials such as ceramics, metals, composites, solid propellants, catalysts, magnets and high-$T_C$ superconductors all constitute particles or "grains" and are manufactured by consolidation of powders. Particle size is one dominant parameter in all these industrial products that dictates their properties and performance. Determination and control of particle characteristics, especially the particle size distribution, are essential for product quality control and performance.

Various methods have been developed in the past to determine the particle size distribution in powders. These range from sieve elimination to laser scattering. Each one of these techniques has its unique advantage and limitations.

The early techniques for characterizing fine particles depended heavily on sieves, elutriators and microscopes. These techniques are time consuming and do not lend themselves to fast and practical measurements. In the period from the mid-1950's to the mid-1970's the methodology of fine particle characterization improved rapidly with the introduction of the instruments as the Coulter Counter, other resista-zone counters and image analyzers. Since mid-seventies the fine particle characterization studies have expanded substantially and many new techniques and instrumentation have been developed. The highlights of this era include holography for characterization of particles in mist and suspension systems; laser Doppler velocimetry (laser-photon correlation spectroscopy) for characterization of particles in aerosols and Brownian motion; eriometry (light/laser diffraction) for evaluating fine particle populations based upon group diffraction patterns; signature-waveform characterization of scattered light for fine particle analysis; fractal description of fine particle profiles; and a new generation of image analyzers with powerful digitization and computer routines for fine particle size and shape analysis.

Most of the recent techniques for particle size determination are based on indirect measurements such as the optical properties of particles obtained from scattering, diffraction, etc., of light or laser directed at the particle surface, or the disturbance of a homogeneous electrical field by a passing particle. If an irregular shaped particle is measured using these physical properties, the "size"of this particle will differ and depend on the particular property chosen. In these techniques, particle size is described by its so-called equivalent diameter, the diameter of a sphere, which yields the same response when analyzing a certain property as the irregularly shaped particle. For these reasons significant differences are found in the particle size distribution results obtained by different commercially available instruments. For measurement of particle size in loose powders the scanning electron microscope (SEM) is a very useful tool because of its superior depth-of-focus compared to optical microscopes. However, use of SEM is extremely time consuming in order to obtain statistically significant measurements. It also needs to operate under vacuum and is not amenable for on-line applications.

On the other hand, none of the current particle-size analysis techniques is applicable to multi-particle mixed solid materials, except for microscopy in certain cases. Microscopy, however, requires destructive sectioning of the solids followed by tedious polishing and etching procedures. These procedures are difficult and time consuming, and sometimes unsuccessful for many ceramics, intermetallics, composites, energetics, and some metals. Particle size analysis of fillers in viscous suspensions (uncured) where the particles are encapsulated is yet another area, which is not feasible even with microscopy.

Analysis of particles in some of the suspensions and solids by these techniques might be feasible only after their constituents are separated effectively. One such technique involves the separation of particles, e.g. separation of solid filler particles from a suspension by heating in an oven to pyrolyze and eliminate the viscous phase. Thereafter, the remaining particulate can be characterized by the known methods. Such intrusive approaches, however, are usually ineffective and expensive.

All the methods mentioned so far, including the early methods, do not provide information on the constitution of the fine particles, i.e., when the fine particles contain more than one material or phase-polymorph, they are not differentiated by these techniques. Scanning electron microscopy (SEM) combined with energy dispersive x-ray fluorescence analysis (EDX) can differentiate compositional differences between the particles in a mixed material. However, SEM with EDX is applicable in general only if the components contain different and contrasting elements that are heavier than oxygen and are not affected by the vacuum. The EDX technique is also limited to submicron thick surface layers and prone to errors due to surface films. Use of SEM with EDX is time consuming and is not amenable for on-line applications.

X-ray diffraction methods can be applied to determine the size of particles in some special cases. Early work has been done with Debye and back-reflection cameras. In these x-ray diffraction techniques particles or grains of a polycrystalline material are irradiated with a collimated beam and diffraction takes place in the coherently reflecting planes of the particles. When large numbers of particles are irradiated under the incident beam, their diffraction spots overlap and form continuous diffraction lines on appropriate Debye rings. Continuity of the rings breakdown and individual diffraction spots are resolved if the number of diffraction particles is reduced. However, the number of diffracting particles is reduced and diffraction spots from individual particles are resolved only if the particle size is very large. Furthermore, these x-ray techniques are very tedious and cannot be applied routinely.

Previous efforts in this area include:

Mack, U.S. Pat. No. 3,148,275 discloses a x-ray technique that is not for particle size analysis. Rather, it relates to a special sample holder to hold a curved specimen to improve wide-angle x-ray diffractometer (WAXRD).

Goebel, U.S. Pat. No. 4,144,450 does not disclose a particle size analyzer, but rather relates to a wide-angle x-ray powder diffractometer equipped with a horizontal linear position sensitive proportional counter (PSPC) for simultaneous data collection from a range of 2θ angles, on the equatorial diffraction plane. This is a regular WAXRD technique with a horizontal linear position-sensitive detector (PSD). This is not a particle size analyzer.

Ladell, U.S. Pat. No. 4,199,678 does not disclose a particle size analyzer. Rather, it relates to a modified WAXRD for texture (preferred orientation) analysis with a point detector.

Rinik. et al., U.S. Pat. No. 4,649,556 discloses an indirect method to get information on the "average" particle size by making use of the variation of diffracted intensity with WAXRD 2θ angle using a point detector. It does not obtain direct information on the particle size and cannot do measurements on individual particles to get particle size distribution.

Cocks. et al., U.S. Pat. No. 4,821,301 discloses a technique for glancing-angle x-ray-absorbance chemical analyses of thin (1000 Å) films. It does not relate to particle size analysis.

Moulai, U.S. Pat. No. 5,128,976 does not disclose a particle size analyzer. Rather, it relates to an oscillation radiographer with a point detector. It is based on absorption contrast and uses a x-ray film to record it. It does not use any of the beam path on the detector system nor the type of data analysis that the present invention (XAPS) uses.

Goebel, U.S. Pat. No. 5,373,544 does not disclose a particle size analyzer. Rather, it relates to an optimized WAXRD designed for the capillary samples. It utilizes a curved mirror to focus the primary x-ray beam and a mobile horizontal linear position sensitive proportional counter with a radial collimator for simultaneous data collection from a range of 2θ angles on the equatorial diffraction plane.

Carpenter, U.S. Pat. No. 5,418,828 does not disclose a particle size analyzer like the present invention disclosed here, where large number of particles, typically 0.51 μm to 300μm in size, can quantitatively be analyzed simultaneously. This technique, rather, is meant for particle imaging for particles 1–2 mm in diameter or larger and generally will not work for powders with smaller particle sizes. It uses a linear position sensitive detector in horizontal configuration as opposed to a vertical configuration of the present invention (XAPS). It uses the diffraction information by scanning to construct a low resolution "image" of a very large particle at one angular setting. In the present invention, diffraction information is obtained from rocking the particles to get the total integrated intensity, which corresponds to total volume/size of the particles, and it is the "integrated intensity" not the "image" that is utilized for particle size analysis.

Hautman, U.S. Pat. No. 5,446,777 discloses WAXRD with a horizontal linear position-sensitive detector that is designed to carry out location—specific WAXRD measurements on a give sample. It does not relate to a particle size analyzer.

Yazici, et al., "Defect Structure Analysis of Polycrystalline Materials by Computer-Controlled Double-Crystal Diffractometer with Position-Sensitive Detector," J. Appl. Cryst. (1983), discloses a computerized double-crystal diffractometer and a position-sensitive detector which analyzes defects in solid specimens.

None of these previous efforts, taken alone or in combination, teach or suggest all of the elements of the present invention, nor do they disclose the advantages of the present invention.

OBJECTS AND SUMMARY OF THE INVENTION

It is a primary object of the present invention to provide a method and apparatus for detennining particle size and particle size distribution of crystalline particles in powders, suspensions and solids non-intrusively without the need to extractor separate the particles from the rest of the material.

It is another object of the present invention to provide a method and apparatus for determining the particle size at rates near real time for on-line process/product quality control applications in various manufacturing operations.

It is another object of the present invention to provide method and apparatus, which can determine particle size distribution of the solid ingredients of formulations involving a plurality of different types of crystalline particles.

It is another object of the present invention to provide a method and apparatus, which can determine particle size distribution of particles in more than one phase or polyrnorph.

It is another object of the present invention to provide a method and apparatus for differentiating between different components of a composite or mixture in determining particle size distribution.

It is another object of the present invention to provide an apparatus for determining the particle size distribution, which includes an x-ray source, a monochromator, a position sensitive detector and computer means for determining particle size distribution.

It is still even another object of the present invention to provide a method and apparatus for determining particle size distribution which rocks a specimen or the x-ray source through the angular range of reflection of the particles at Debye arc or portion thereof.

These and other objectives are achieved by the apparatus of the present invention, which comprises a x-ray source, a monochromator, a goniometer, a position sensitive detector and computer means for interpreting the data obtained at the position sensitive detector. The method of the present invention includes the steps of generating an x-ray; narrowing the wavelength of the x-ray by means of a monochromator; placing a specimen in the path of the x-ray beam; allowing the particles to diffract the beam; detecting the diffracted beam with a position sensitive detector; collecting the diffraction data from individual particles; rocking or rotating the specimen or the x-ray source for successive times to cover the angular range of reflection of the particles; compilation of the diffraction data in the computer memory to construct the intensity profile for individual particles; and interpreting the data to determine particle size and distribution of crystalline particles.

By the method and apparatus of the present invention, particle size and particle size distribution of crystalline particles in powders, suspensions and solids can be determined upon collection of samples from a process and characterization off-line at another location with the apparatus and method of the present invention, or on-line with the process using the apparatus and the method of the present invention. Importantly, the present invention allows for these determinations to be made in situ, without the need for separating the particles, and sufficiently fast so that the generated data can be used in a process control algorithm for quality and process control.

BRIEF DESCRIPTION OF THE DRAWINGS

Other important objects and features of the invention will be apparent from the following Detailed Description of the Invention taken in connection with the accompanying drawings in which:

FIG. 11a contains the results of scanning electron microscopy (SEM) measurements, Frequency (number percent) vs. Particle size (microns), and FIG. 11b reports the results of X-ray Analyzer for Particle Size (XAPS) measurements, Frequency (number percent) vs. Intensity (photons per second).

FIG. 12a contains the results of scanning electron microscopy (SEM) measurements, Frequency (number percent) vs. Particle size (microns), and FIG. 12b reports the results of X-ray Analyzer for Particle Size (XAPS) measurements, Frequency (number percent) vs. Intensity (photons per second).

FIG. 14a contains the results of scanning electron microscopy (SEM) measurements, Frequency (number percent) vs. Particle size (microns), and FIG. 14b reports the results of X-ray Analyzer for Particle Size (XAPS) measurements, Frequency (number percent) vs. Particle size (microns).

FIG. 15a is a SEM photomicrograph of "fine" HNIW powders at 2000× magnification and FIG. 15b is a SEM photomicrograph of "coarse" HNIW powders at 300× magnification.

DETAILED DESCRIPTION OF THE INVENTION

The present invention comprises a novel method and apparatus that can effectively measure the "true" size of individual crystalline particles, with the diffraction information that is directly proportional to particle mass, and determine the particle size distribution characteristics in loose powders, suspensions, and solids. The technique can also differentiate the particles of the multiple ingredients in a given mixed state and quantitatively measure the particle size distribution and the relative volume fraction and phase or polymorph of each component. The method and apparatus of the present invention can be used to determine the particle size of individual crystalline and semi-crystalline particles including powders, grains and whiskers, in loose powders, particle-filled viscous suspensions and multi-particle solid materials. The present invention is a non-invasive technique that requires minimum sample preparation. Measurements can be carried out in ambient atmosphere without the need for the application of vacuum, carrier fluids or other medium. Each measurement may take only a few minutes of time or less depending on the sample material and may even be performed "on-line" at production facilities.

Figure 1:
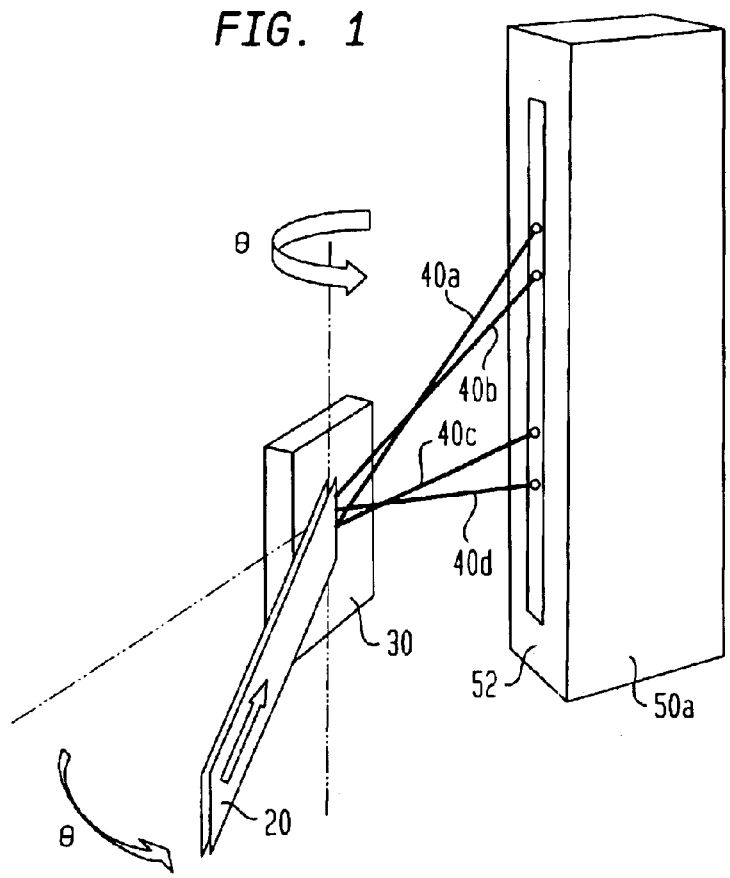
FIG. 1 is a schematic view of the present invention, X-ray Analyzer for Particle Size (XAPS), equipped with a linear position-sensitive detector positioned perpendicular to the equatorial diffraction plane and a rocking multiparticle specimen or x-ray beam.

Referring to FIG. 1, it can be seen that a monochromatic x-ray beam 20 is directed at a specimen 30 and impinges on particles comprising the specimen which causes a diffraction of the x-ray beam indicated at 40a, 40b, 40c, and 40d emanating from particles a, b, c, d on the specimen. These diffracted beams 40a–40d are picked up by position sensitive detector 50a, through entry slit 52. The azimuthal position $\psi$ on the Debye arc, which is made to coincide with the length of the PSD, is identified and the intensity I is measured as graphically shown in FIG. 2. A computer means is utilized to interpret the data from the position sensitive detector 50a.

Although the XAPS unit utilizes a highly parallel crystal monochromatization where the monochromator can be symmetrically or asymmetrically cut, flat or curved, single, two-parallel or channel-cut crystals, other means of obtaining highly parallel monochromatic beam are also considered. For example, combined use of filters, curved mirrors, tapered capillaries or parallel and monochromatic sources such as accelerators, plasmadischarge units or a synchrotron source can all be used.

This setup for the present invention is carried out in a high precision $\theta$—$\theta$ diffractometer and includes a x-ray source, a $\theta$—$\theta$ goniometer for rotating the sample or the x-ray source, and a detector such as a position sensitive detector 50a. Additionally, a monochromator, such as a crystal-monochromator and various slits, collimators and capillaries may be used to obtain a highly parallel monochromatic x-ray beam 20 having very narrow wavelength. X-ray film, a position sensitive detector, or a CCD camera can be used to detect and differentiate the diffraction of the monochromatic x-ray beam from the individual particles of the specimen.

Figure 2:
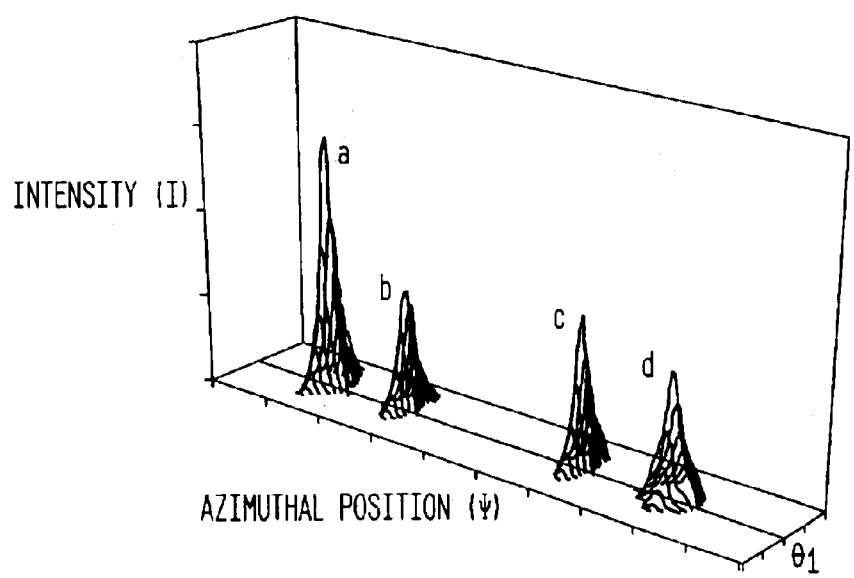
FIG. 2 is a graph of intensity versus azimuthal position $\psi$ on a Debye arc obtained by the X-ray Analyzer for Particle Size (XAPS) configuration in FIG. 1.

The present invention is based on double-crystal diffractometry method, where individual particles are regarded as the second or test crystal of the double crystal diffractometer. During measurements, the particulate sample or the x-ray source may be oscillated, rotated or rocked for a sum of several tens of minutes of arc about the Bragg angle, while being irradiated by a crystal or otherwise monochromated parallel x-ray beam. Several particles (or grains) in the sample will be in Bragg reflecting positions which result in individual microscopic diffraction spots along the appropriate Debye arc. These spots are detected by a position-sensitive detector (PSD) either linear 50a and oriented parallel to the Debye arc or a two-dimensional 50b PSD, or a CCD camera or a fiber-optic detector or an image plate or a film or any other two dimensional position sensitive detector system. These principles of operation of the XAPS method and the diffraction peaks obtained are schematically shown in FIGS. 1 and 2 for one dimensional detectors 50a, and in FIGS. 3 and 4 for two dimensional detectors 50b. The intensity distribution of each diffraction spot of an individual particle and its location and distribution are then stored in a computer for subsequent numerical analysis (see FIG. 5). The integrated intensity of an individual diffraction spot is directly proportional to the volume and mass of the particular diffracting particle in the sample.

The primary x-ray beam 20 can be monochromatized in a number of ways like diffraction from the planes of a flat or channel-cut crystal. Upon monochromatization the resultant monochromatic beam has a very small horizontal convergence and is nearly parallel, while the vertical divergence of the beam is controlled by a slit, collimator or capillary systems. In one embodiment of the invention the sample under investigation is mounted on a two-dimensional microscope stage which enables precise selection of the region of interest. The axis of the sample holder is rotated by a stepping motor for orienting along an appropriate angle. Various detectors including a one-dimensional position-sensitive detector, which is located parallel to the Debye arc, a two-dimensional position sensitive detectors a CCD camera or a fiber-optic detector or an image plate or film or any other two-dimensional position sensitive detection system can be used. A typical source, i.e., 0.5–3 kW diffraction tube with a Cu target may be used as the x-ray source, however, other sources including rotating anode sources using Cr, Mo or other targets that generate softer or harder x-rays are useable. Each measurement may take up to a few minutes. The speed and resolution can also be enhanced, if necessary.

The present invention can typically analyze particles ranging in size from 0.5 $\mu$m to 300 $\mu$m in diameter, without altering its x-ray optics. These limits however, can be expanded by making appropriate changes in the x-ray optics. For example, by use of a microfocus x-ray source and/or a tapered capillary to focus the incoming beam, the lower limit of the particle size analysis can be further lowered from 0.5 $\mu$m. And, conversely, by use of a harder (shorter wavelength) x-ray beam and calibrated collimator/slit systems the upper limit in the particle size analysis can be further increased from 300 $\mu$m to several millimeters.

As an additional embodiment of the invention, the vertical and horizontal divergence of the monochromatic beam can be adjusted, for example, by adjustable slits, for vertical and by use of asymmetric crystals, for horizontal divergence, and through such alterations of the x-ray optics the width of the beam divergence can be tuned with that of the angular-range-of-reflection of the given particles, and this way the particle size can also be determined from a single exposure without rocking the sample or the beam.

Figure 6A:
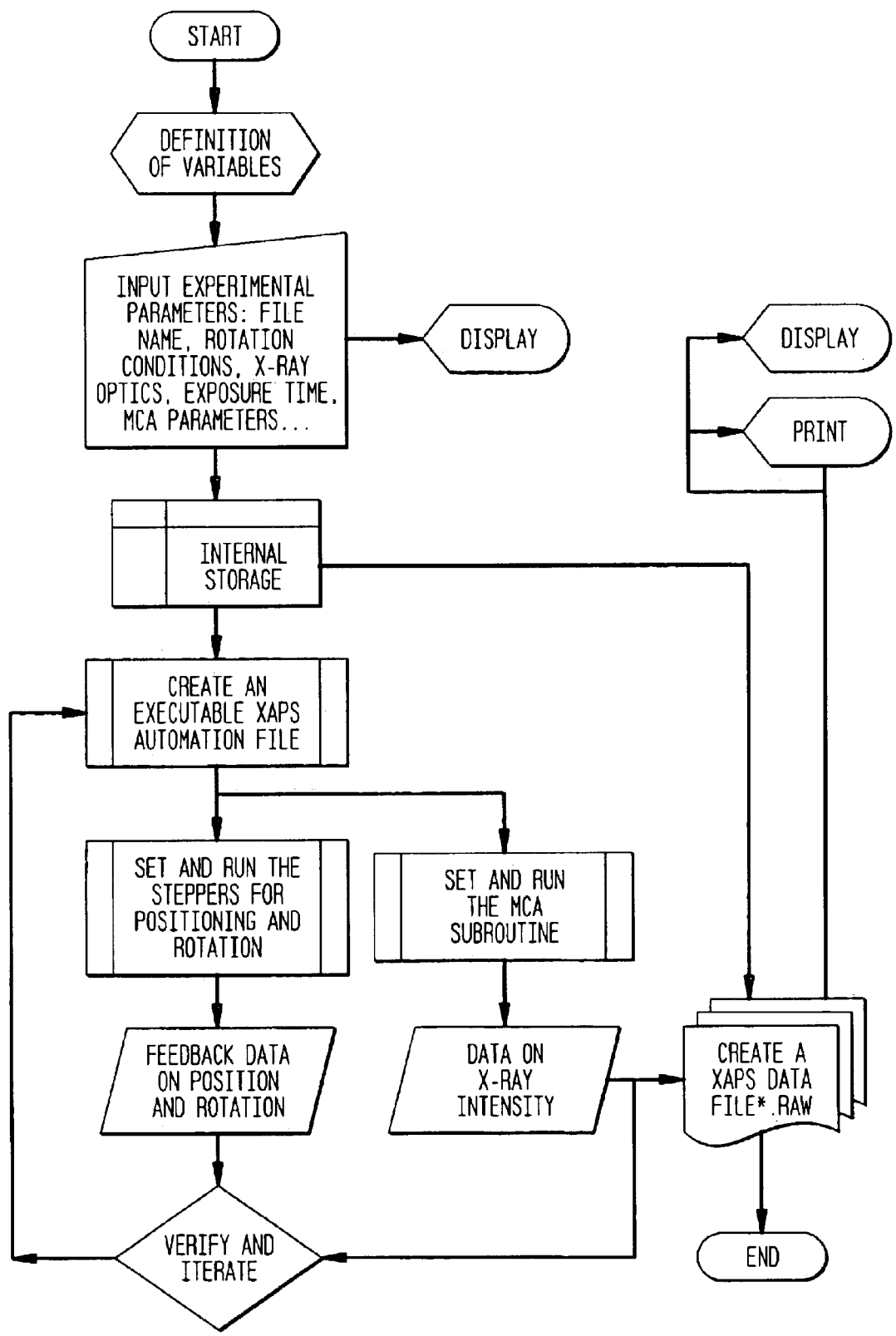
FIG. 6(A)–6(C) are flow charts showing the basic steps of the two computer programs used in connection with the invention, for data collection and analysis.
Figure 6B:
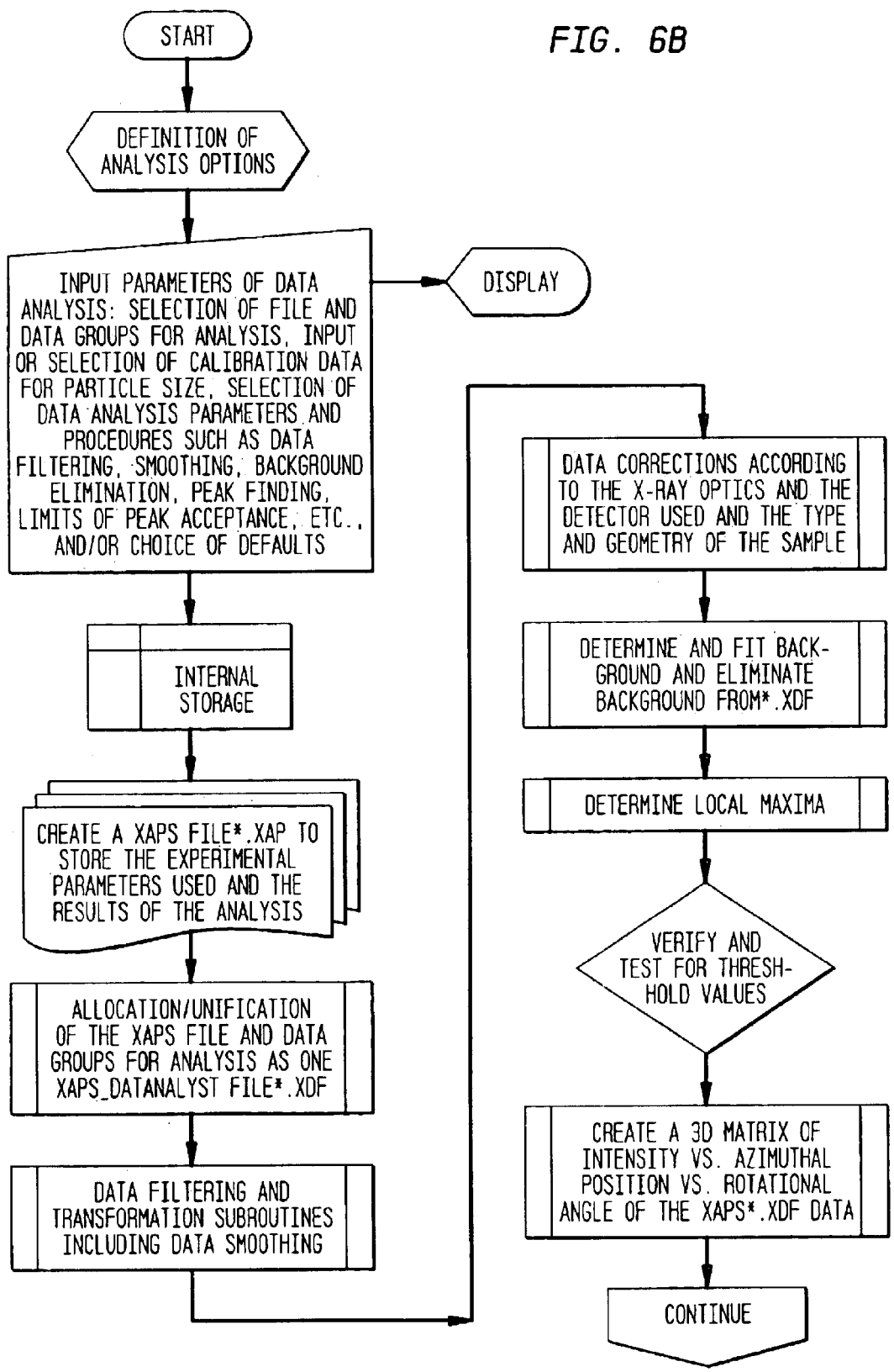
Figure 6C:
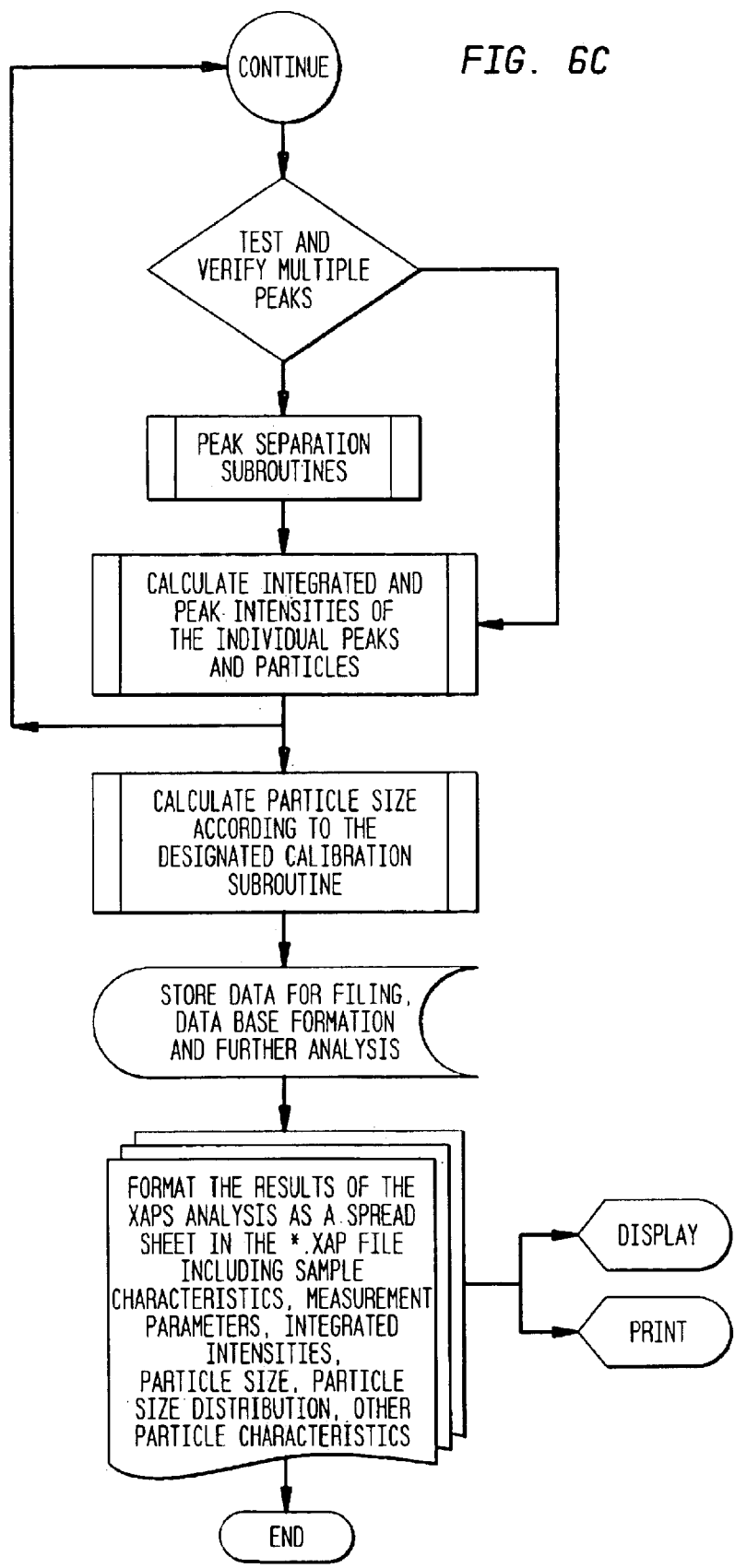

Flow charts of programs used in the present invention are shown in FIGS. 6(A)–6(C). The programs are used to determine the particle size/intensity/distribution and utilize algorithms for data interpretation, background correction, peak and integrated intensity determination and statistical analysis and graphics for the deduction of particle size distribution parameters. These include: 1) a program (XAPS DATA COLLECT), FIG. 6A, that has been developed for automation of the moving parts in the XAPS apparatus and for data acquisition; and 2) a program (XAPS DATANALYST), FIGS. 6(B) and 6(C) for data analysis to determine the particle size/intensity/distribution, including a set of algorithms for data interpolation, background correction, peak and integrated intensity determination and statistical analysis and graphics for the deduction of particle size and microstrain distribution parameters.

Figure 4:
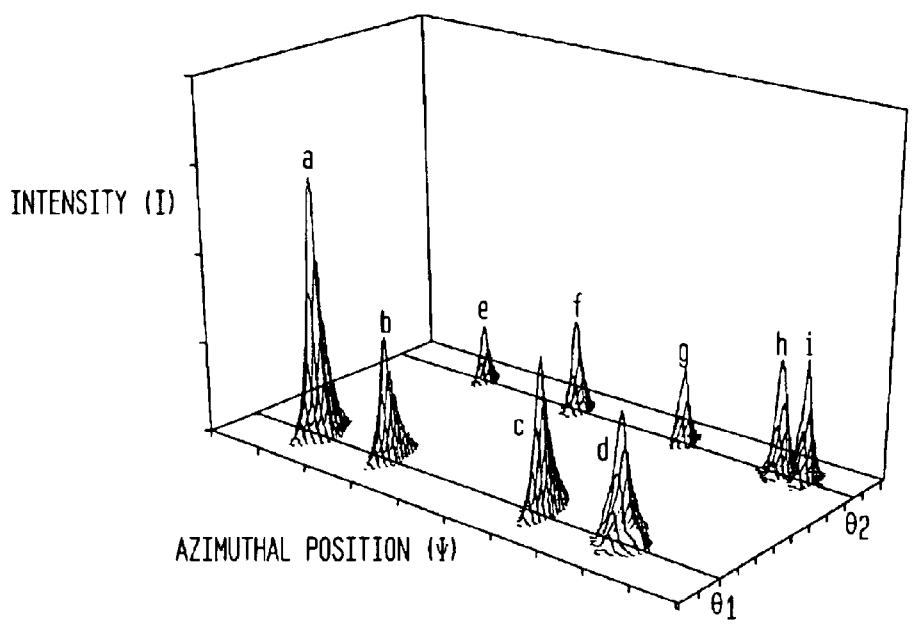
FIG. 4 is a graph of intensity versus azimuthal position $\psi$ on two Debye arcs versus the angular position $\theta$ obtained by the X-ray Analyzer for Particle Size (XAPS) configuration in FIG. 3.
Figure 5:
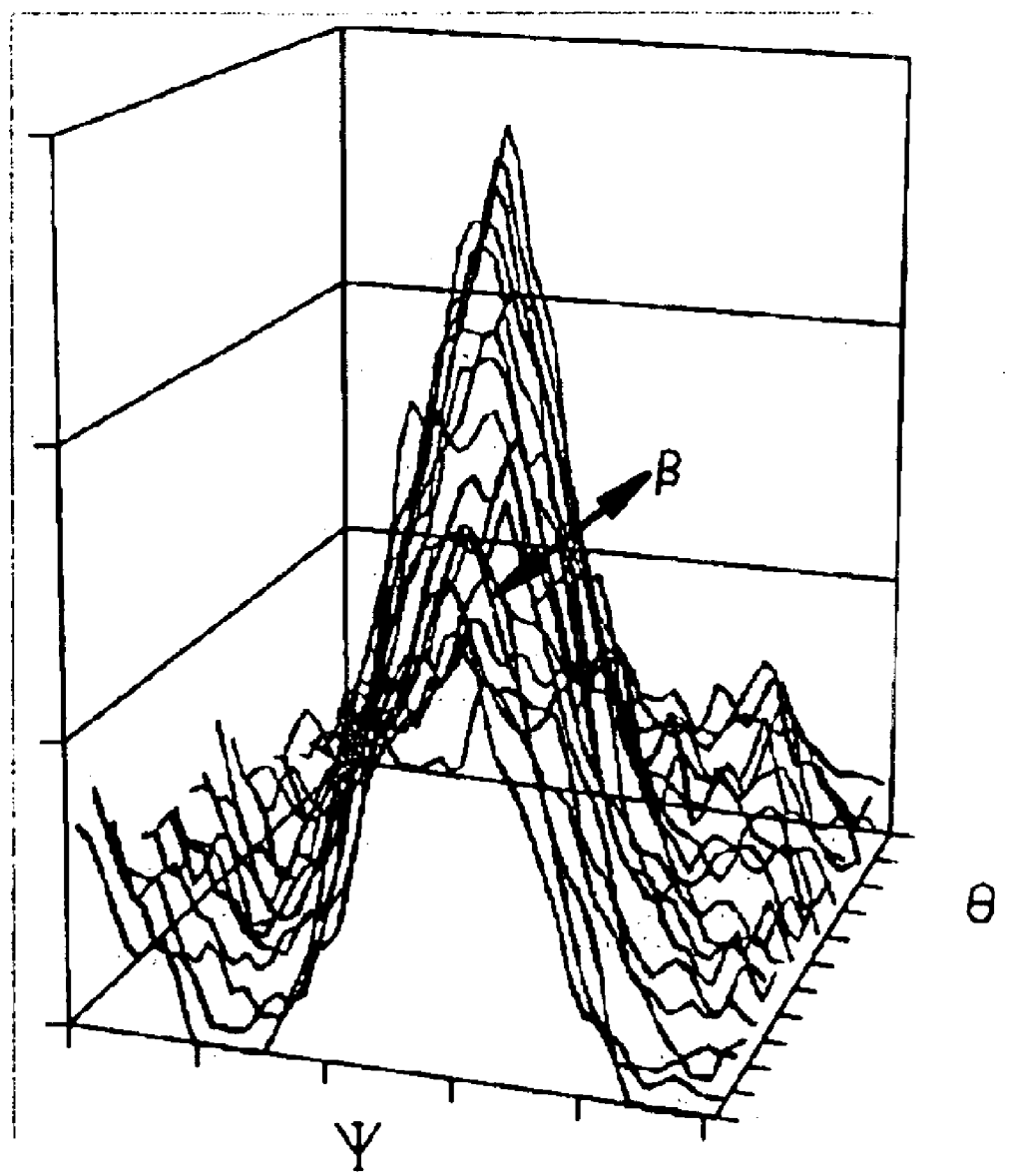
FIG. 5 is a graph of a typical X-ray Analyzer for Particle Size (XAPS) data for a single particle.

In one embodiment the x-ray intensity spectra of multiple particle reflections are collected and displayed, as shown schematically in FIGS. 2 and 4, by a multichannel analyzer (MCA) and a computer. Subsequently, the spectra from individual particles are stored in the computer as shown in FIG. 5 for further analysis. A large particle population can readily be analyzed at each region of interest by taking multiple exposures at the Bragg angle. Also, the entire sample surface can be analyzed by moving the sample with a microstage relative to the incident beam.

If no control experiments are possible the intensity values have to be corrected for absorption. The integrated intensity of the diffraction from an individual particle is directly proportional to the volume of the particle. The intensity is given by:

$$I=I_0K/r^2|F|^2p(l+\cos^2 2\theta)/(\sin^2\theta\cos\theta)A(\theta)e^{-2M} \quad (1)$$

Where, I: diffracted beam intensity, $I_0$: incident beam intensity, K: constant, r: distance from the diffraction site, F: structure factor (material dependent), p: multiplicity factor (material dependent), $\theta$: Bragg angle (material and x-ray wavelength dependent), A ($\theta$): absorption factor (material, x-ray wavelength and (particle) size and shape dependent), $e^{-2M}$: temperature factor. The absorption factor is given by:

$$A(\theta)=A(hkl)=1/V\exp\{-\mu(p+q)\}dV=1/A^* \quad (2)$$

Where, h, k, l: Miller indices, V: volume (of the particle), $\mu$: linear absorption coefficient (material and x-ray wavelength dependent), p and q: the lengths of the paths of the incident and reflected beams in the material ($\theta$ and particle size and shape dependent), A*: correction factor for absorption to get the "true" intensity.

Figure 7:
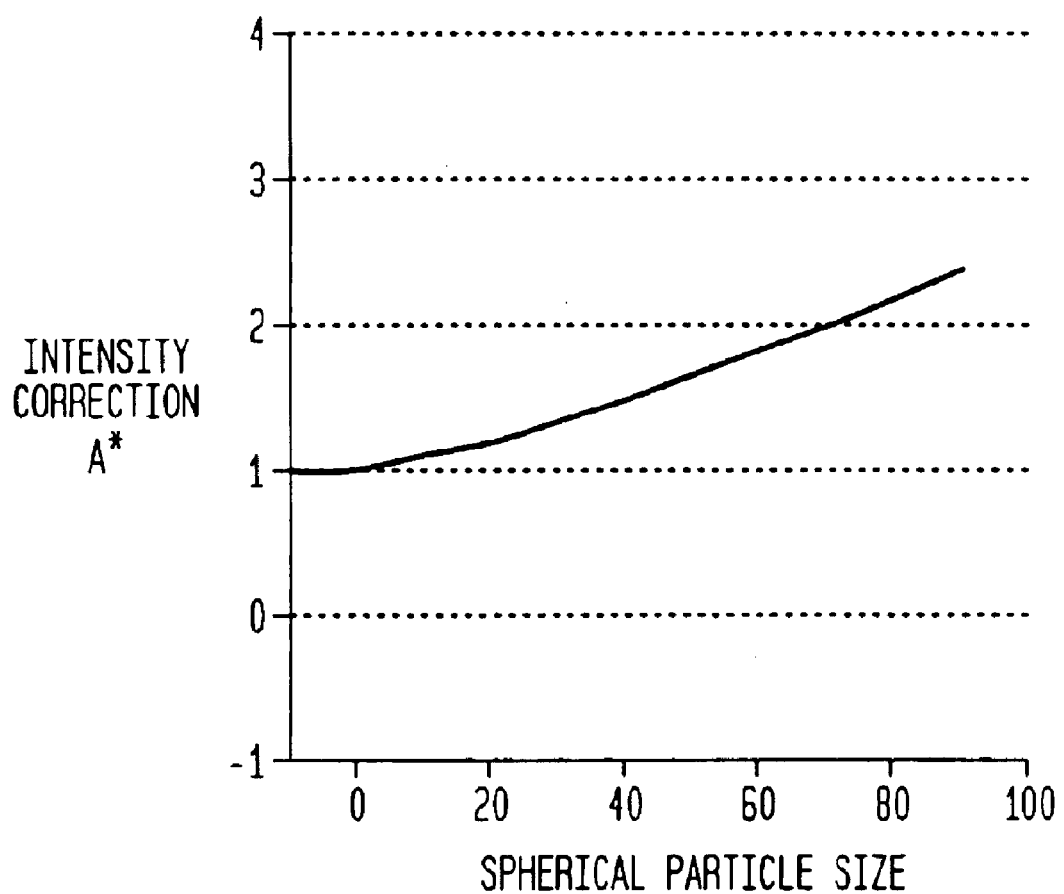
FIG. 7 is a graph of absorption correction factors for spherical aluminum particles and Cu K-$\alpha$ radiation versus the particle size.

According to equations 1 and 2, the relationship between the intensity and the particle mass/volume deviates from linearity depending on the absorption characteristics of the monochromatic x-rays for the given material that is being tested. A correction function has to be applied in order to obtain the "true" intensity and the "true" particle volume from the intensity values. For a multitude of materials the correction factors, A*, are given in a normalized format in International Tables for X-ray Crystallography. These calculations are possible for a few regular particle shapes such as an ideal sphere or a cylinder. Such calculations were carried out for a spherical aluminum particles and CuK$\alpha$ radiation. The results of this work are shown in FIG. 7. However, majority of the powders contain particles with irregular shapes, and in order to achieve high accuracy in the particle size versus intensity correlations, a one-time calibration measurement needs to be carried out, preferably with scanning electron microscopy (SEM) for the particle size of the same material.

The present invention is applicable to particles which are crystalline or highly amorphous particles and particles with excessive plastic deformations cannot be analyzed by this method and apparatus.

Figure 8:
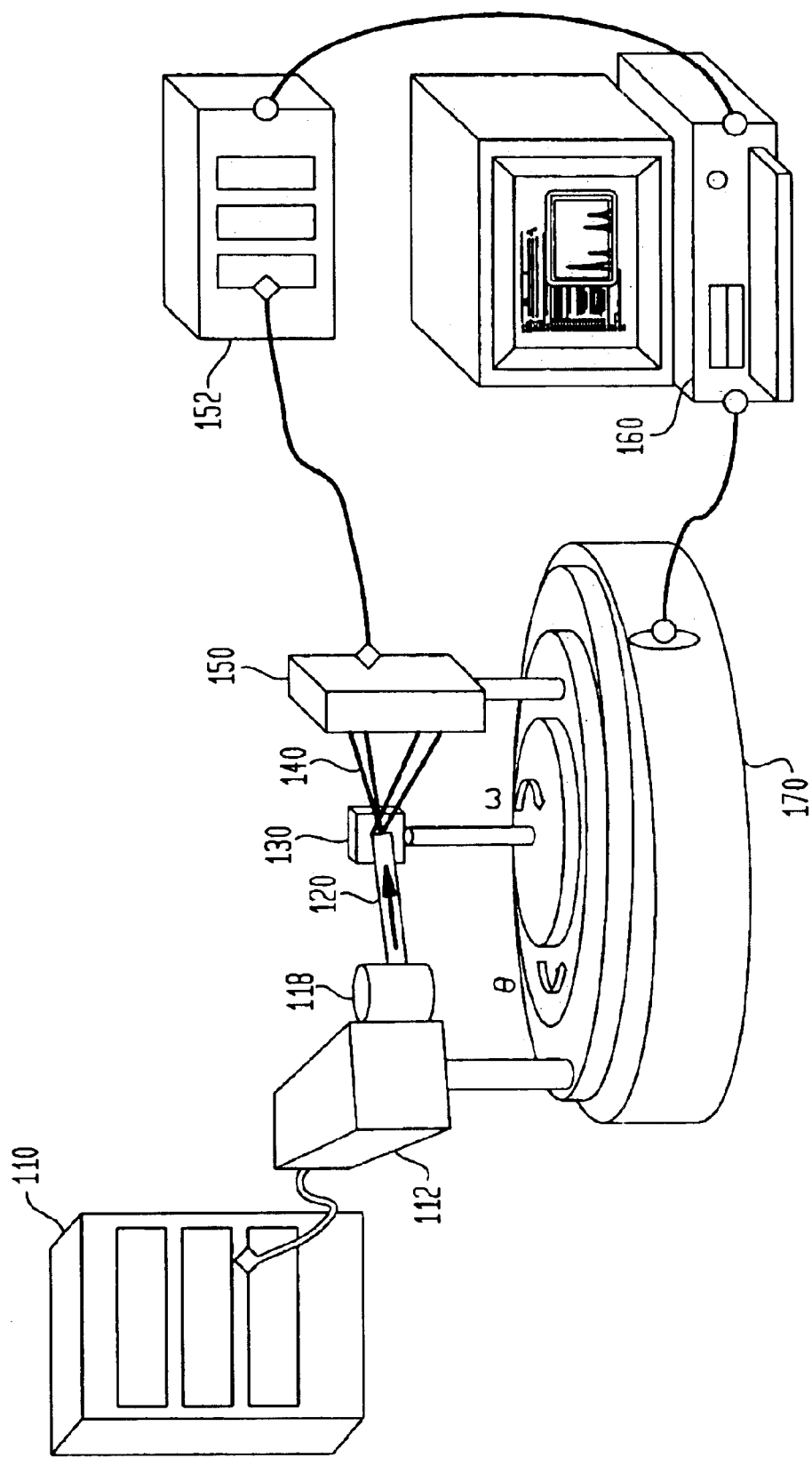
FIG. 8 is a block diagram of the apparatus used in this invention.

A block diagram of the XAPS system of the present invention, for off-line applications, is shown in FIG. 8 The x-ray source for the system could be a rotating anode or a sealed x-ray tube 112 with its high-voltage supply 110. These x-ray generators are available from numerous manufacturers. The ones currently utilized are a Rotaflex rotating anode system by Rigaku, Danvers, Mass., and a XRD-6 sealed-tube system by General Electric, Schenectady, N.Y.

A monochromator 118 and a θ—θ-ω goniometer 170 currently used is made by Picker model 3488L. Similar goniometer and monochromators are also available by Huber, Blake Industries, Scotch Plains, N.J. Currently a flat symmetric-cut Si(III) single crystal and an asymmetric-cut Si (III) crystal are used in the monochromator 118 to obtain a monochromatic parallel beam 120. This beam 120 is diffracted by particles in the sample 130 to create diffracted beam 140.

The Picker unit has been retrofitted with a stepping motor system for automation: model M092-FC08 motor by Superior Electric, Bristol, Conn., and a stepper control model DPH37 by Anaheim Automation, Anaheim, Calif. Sample rotation/rocking step of 0.1 minutes of arc about angles θ, ω, is made possible with this system. For the off-line XAPS system shown in FIG. 8, only the sample 130 is rotated or rocked. The x-ray source 112 and the position sensitive detector (PSD) 150 are held stationary.

There are two linear PSD 150 and related PSD electronics 152 systems that are used in the current invention. One PSD system is manufactured by TEC, Knoxville, Tenn., Model 200-PD-01 detector and Model 200-DM-01 signal processing electronics. The other PSD system is manufactured by M Braun, Garching, Germnany, Model PSD-50M and Model ASA-5 electronics.

The computer 160 used for automation of the goniometer 170, data acquisition from the PSD electronics 152 and for data analysis, is an IBM-PC type computer 486 or better, available from numerous manufacturers. For data acquisition, the signals from the PSD electronics module 152 are captured by a multi-channel analyzer (MCA) PC-board installed in the PC. Currently, two MCA boards are being utilized, both manufactured by EG&G Ortec, Oak Ridge, Tenn. The boards are Model Trump-2K and Model Trump-8K-W3, respectively.

Figure 9:
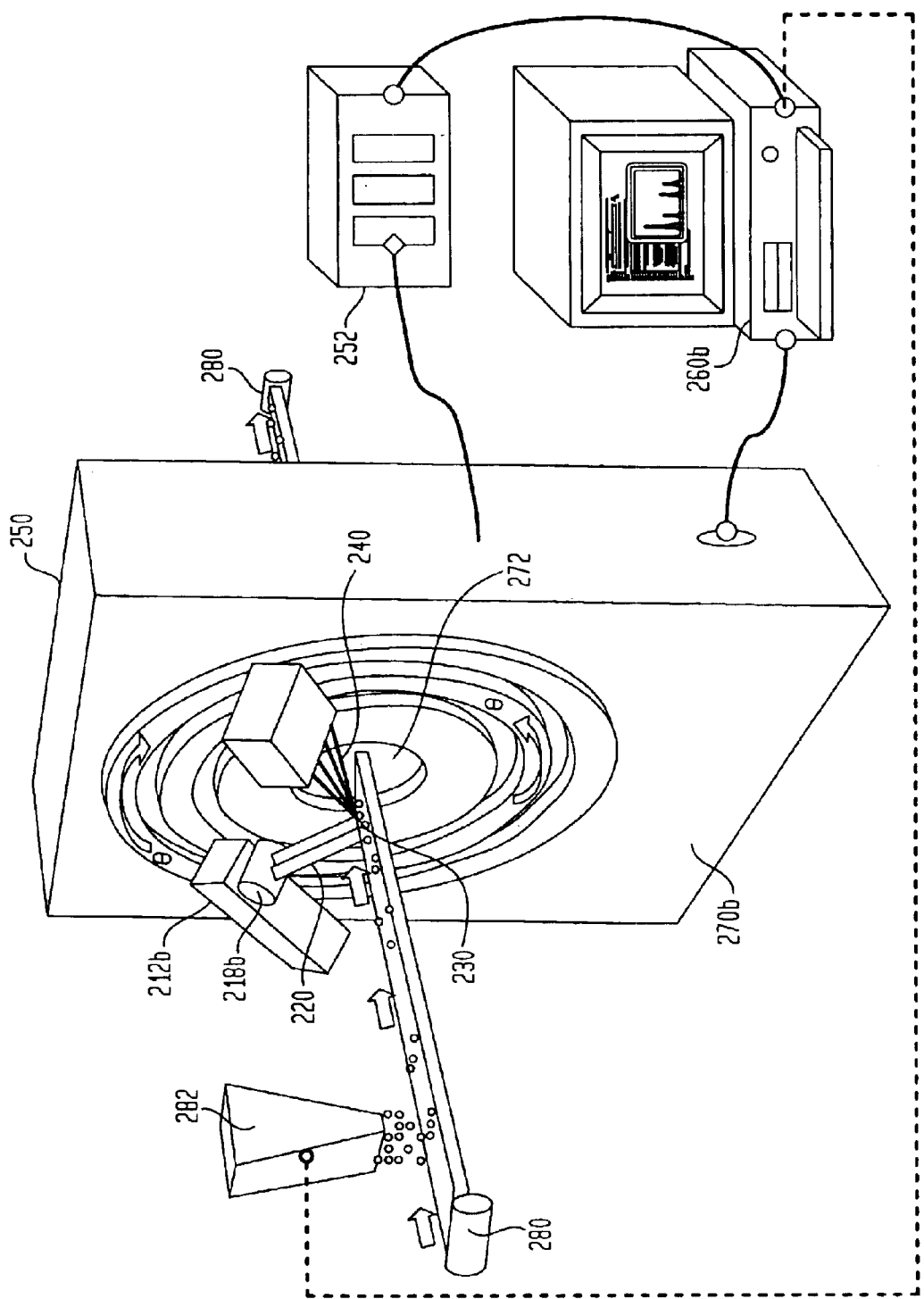
FIG. 9 is a block diagram of a modified apparatus for performing the present invention in real or near-real time, as part of the production process.

A block diagram of the XAPS system of the present invention for on-line applications is shown in FIG. 9. The on-line version is designed and built for carrying out particle size distribution analysis in processing and manufacturing environments, on-site and on-line with the processing equipment 282 so that manufactured products such as powders, powder-binder suspensions or powder binder solid articles are analyzed immediately for quality control. Currently, conveyor system 280 in FIG. 9, Model 2100 by Donner, Hugo, Minn., is employed to bring the sample material to the correct position at the center of the x-ray unit 270b. In this way, particle size distribution of particles found in the powder, suspension or solid forms may be analyzed sequentially. The measurements are done intermittently where the conveyor is brought to a halt for each sampling during XAPS measurements. The goniometer 270b employed for on-line analysis is a vertical theta-theta goniometer Model D8 manufactured by Bruker, AXS, Madison, Wis. The goniometer has a circular opening 272 in the middle to accommodate the conveyor to pass through, see 280 passing through 270b in FIG. 9. The x-ray source 212b in this version comprises a sealed-tube x-ray generator. In the theta-theta optics, the x-ray source 212b rotates/rocks with theta (θ) motion instead of the sample. The sample is not rotated, but held stationary, in this on-line version of XAPS, making it possible to deliver and analyze samples in as-processed condition. The monochromator 218b includes a curved x-ray mirror for focusing and to obtain a higher x-ray intensity. The beam 220 is diffracted by particles in the sample 230 to create a diffracted beam 240. The PSD system 250 and 252 is made by M Braun as previously set forth.

The computer means 260b used in the on-line version of XAPS is designed to handle additional tasks compared to the off-line version. In addition to the automation of the goniometer, data acquisition from PSD and data analysis, the computer means of the on-line version is able to do near-real time analysis by multi-tasking and also the on-line version is capable of controlling the conveyor 280 motion and communicating with the processing equipment 282 for feedback and quality control tasks.

In a further embodiment of the invention the x-ray unit can be made to move at the same linear speed as the conveyor to allow the determination of the particle size without interrupting the flow of the process streams.

In yet another farther embodiment of the invention the x-ray unit can be kept fixed but the data acquisition system can be programmed to "follow" the moving particles on the conveyor to allow the determination of the particle size without interrupting the flow of the process streams.

To demonstrate the present invention, particle size measurements were carried out on three aluminum powders, which were processed by gas-atomization from melt, and all three constituted near-spherical particles. The average particle size of two of the powder grades were specified by the manufacturer, Ampal, Inc., as 8 μm and 55 μm, respectively and were used as the calibration samples. The "Third" aluminum powder lot with an unknown particle size distribution was used as test material.

A double-sided conductive carbon adhesive tape was used as the mounting medium to hold the loose powder during the x-ray diffraction and scanning electron microscopy (SEM) measurements. Particles were spread on the tape in a monolayer for stability and ease of SEM image analysis.

Figure 10A:
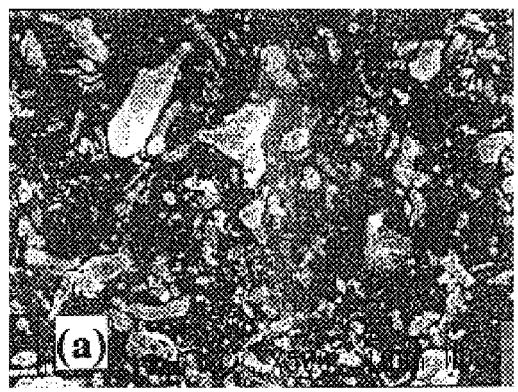
FIGS. 10a, 10b, and 10c are photomicrographs of the (a) "First," (b) "Second" and (c) "Third" samples of the atomized aluminum powders obtained by scanning electron microscope (SEM) at 500×magnification.
Figure 10B:
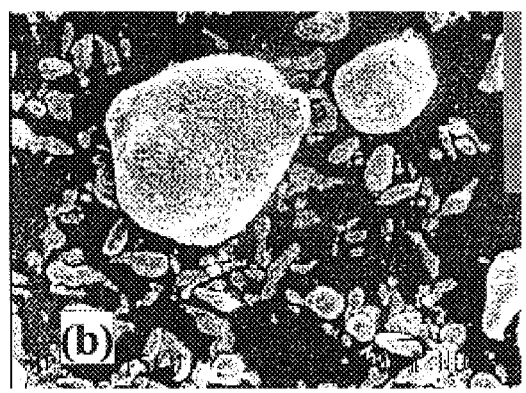
Figure 10C:
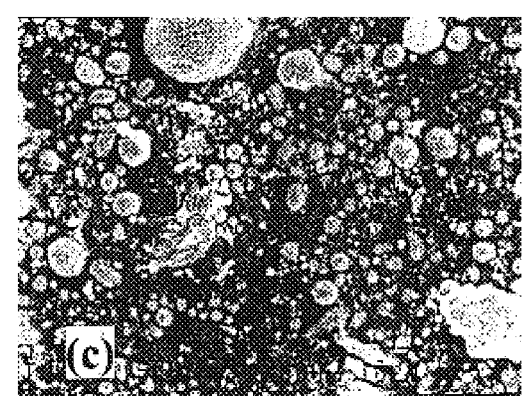

Control measurements of particle size distribution were carried out with a scanning electron microscope. The typical SEM photomicrographs of the three atomized aluminum powders are shown in FIGS. 10a, 10b, and 10c. As shown in FIG. 10, all three powders exhibit nodular particles with rounded nearspherical features which are typical of gas-atomization-from-melt powder processing. In this technique, the secondary electron images of the particles were photographed at high magnification and images were analyzed for particle size determination. An image analysis software was employed for these studies.

Figure 11A:
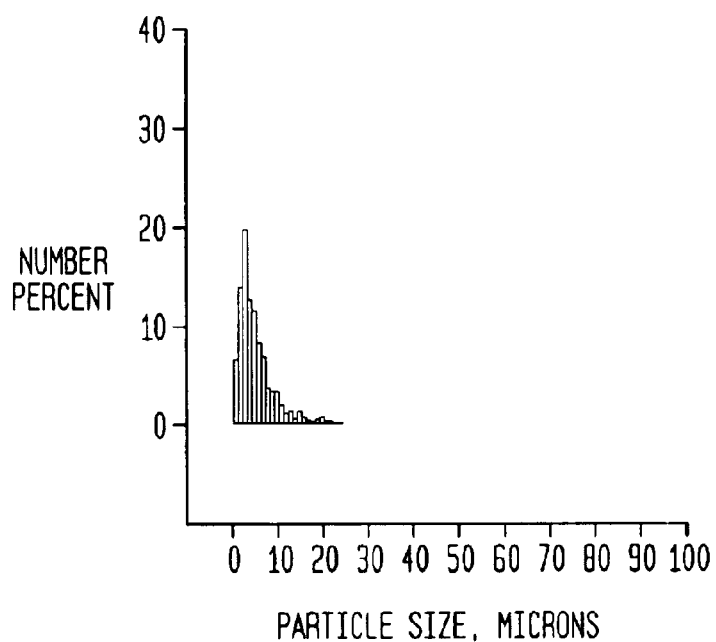
FIGS. 11a and 11b are graphs of the "First" sample of atomized aluminum powder.
Figure 11B:
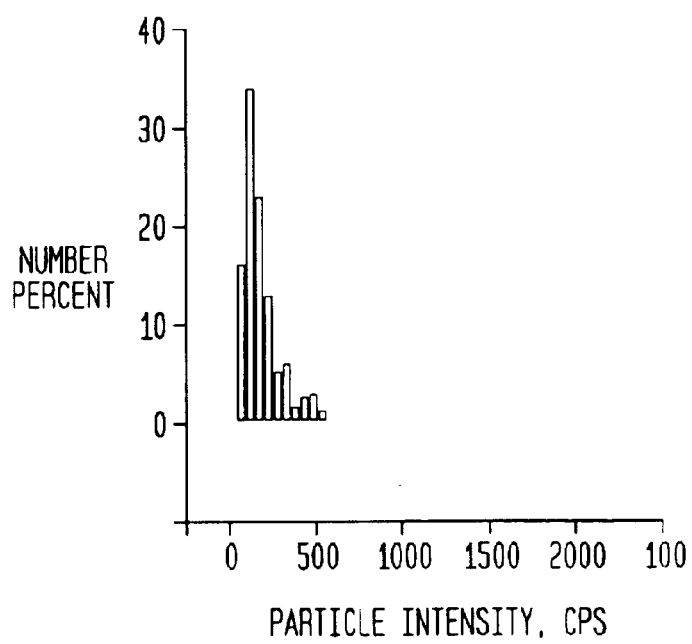
Figure 12A:
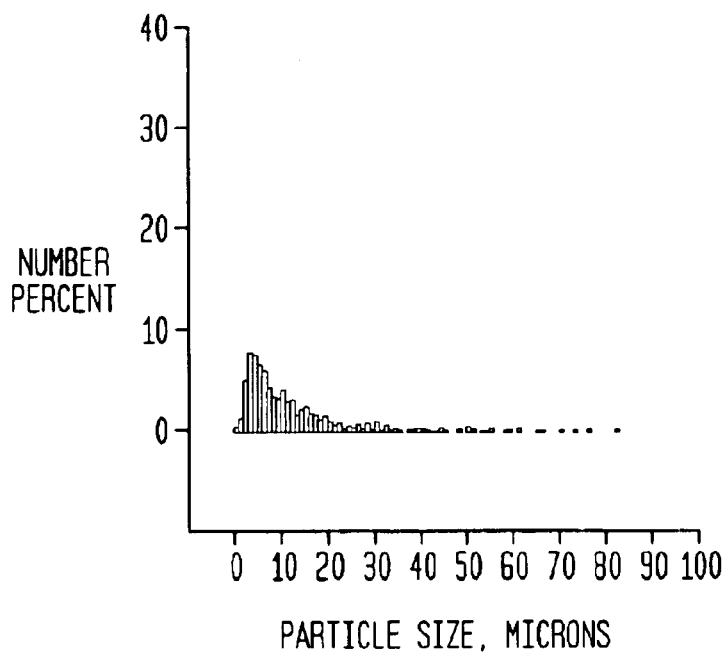
FIGS. 12a and 12b are graphs of the "Second" sample of atomized aluminum powder.
Figure 12B:
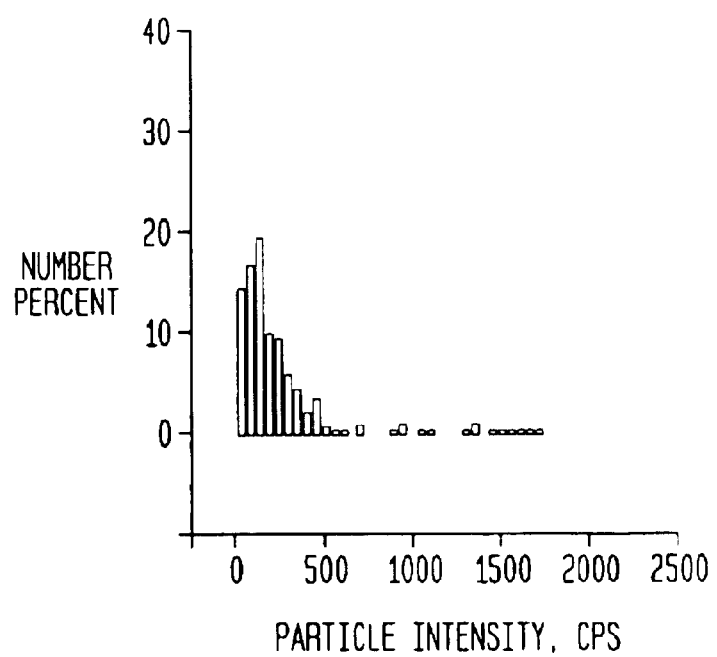

The results of the particle size distribution measurements of the "First"and "Second" aluminum powders are graphically shown in FIGS. 11 and 12, respectively. In FIGS. 11 and 12 the results of both, (a) SEM, and, (b) the XAPS particle size distribution measurements are given for comparison. The SEM results are given in frequency (percent of total number of particles) versus particle size (microns). The XAPS results are given in frequency (percent of total particle number) versus x-ray diffraction intensity from individual particles (number of photon counts per second, cps). As can be seen in FIGS. 11 and 12, the frequency distributions of the intensity values of the present invention are in very good agreement with the frequency distribution of the SEM particle size values since intensity is directly related to particle mass and size.

Figure 13:
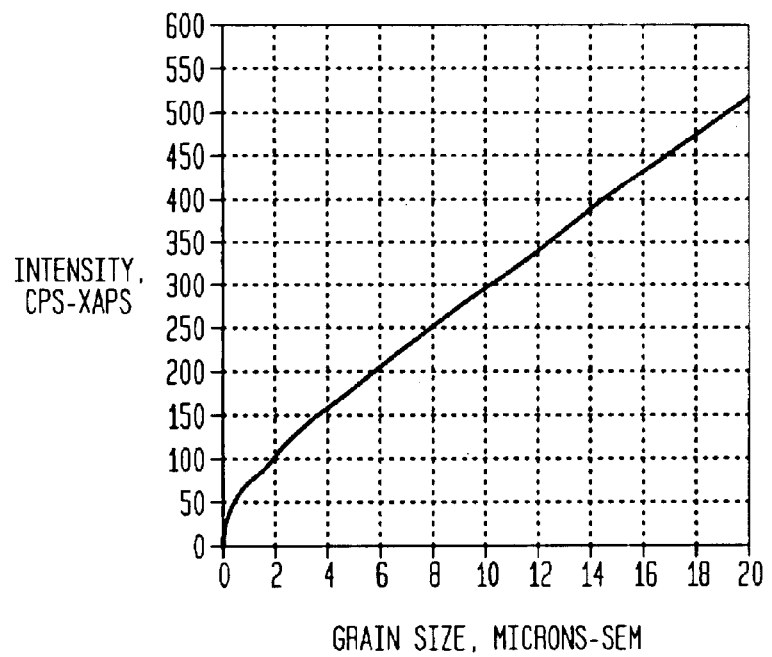
FIG. 13 is calibration curve for conversion of X-ray Analyzer for Particle Size (XAPS) intensity values obtained from aluminum particles to X-ray Analyzer for Particle Size (XAPS) particle size values.

These results of the "First" and "Second" aluminum powders, i.e., the mean, mode, maximum and minimum values and other statistical distribution characteristics (FIGS. 11 and 12) were utilized to calibrate (or train) the XAPS technique for the particle size distribution analysis of the aluminum powders. Through this work a calibration curve for the intensity values was obtained, with respect to the SEM particle size values. This calibration curve is given in FIG. 13. By using this calibration curve the intensity values obtained from another aluminum powder, with unknown particle size distribution, was converted to particle size values, by carrying out the measurements under identical x-ray optics conditions.

This calibration procedure was put to test with the "Third" aluminum powder sample. The results of this work, the particle size distribution of the "Third" sample measured by the present invention are given in FIG. 14a, where, the SEM results from the same sample are also shown for comparison in FIG. 14a. As evident in FIG. 14, the particle size distribution values obtained by the present invention and SEM methods are in very good agreement. Minor differences observed between the two methods are within the expected experimental error of each technique. "Third" powder exhibits close to a bimodal particle size distribution as evident in the SEM photomicrograph in FIG. 10c. This near bimodal characteristics of the particle size distribution of the "Third" powder was successfully determined by the present invention (see FIG. 14b). The average particle size by number values obtained with the present invention and SEM methods were seven microns and five microns, respectively. These results are in very good agreement considering that the particle size distribution of this "Third" sample extends from 0.5 $\mu$m to 40 $\mu$m.

Figure 16:
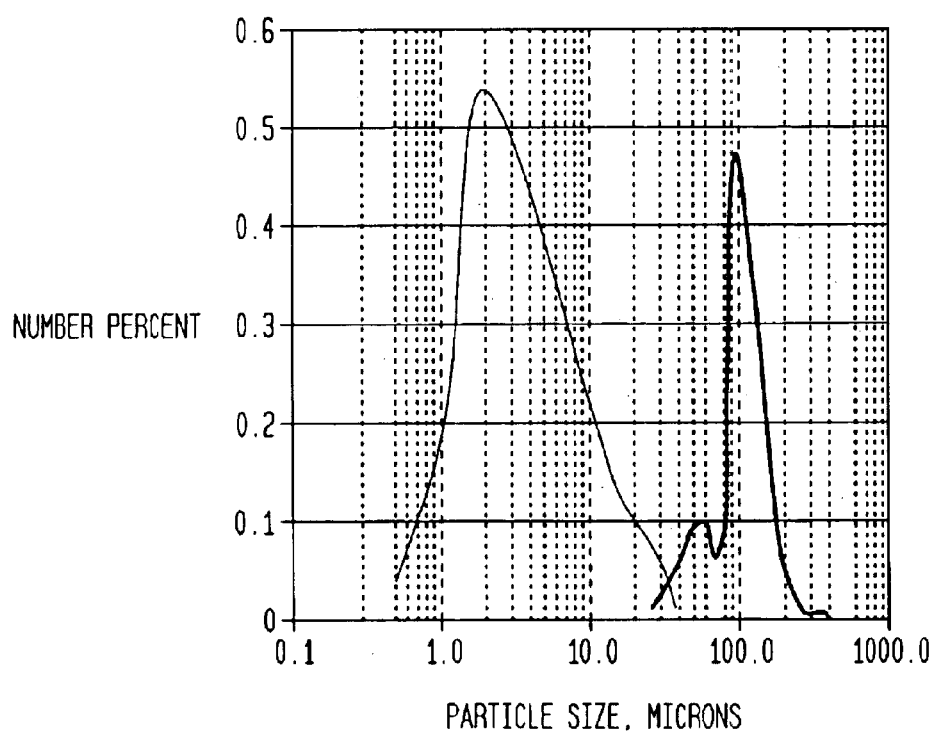
FIG. 16 is a graph of particle size distribution of the "fine" and "coarse" HNIW powders shown in FIGS. 15a and 15b, as measured by the X-Ray Analyzer for Particles (XAPS), frequency (number percent) verses particle size (microns).
Figure 14A:
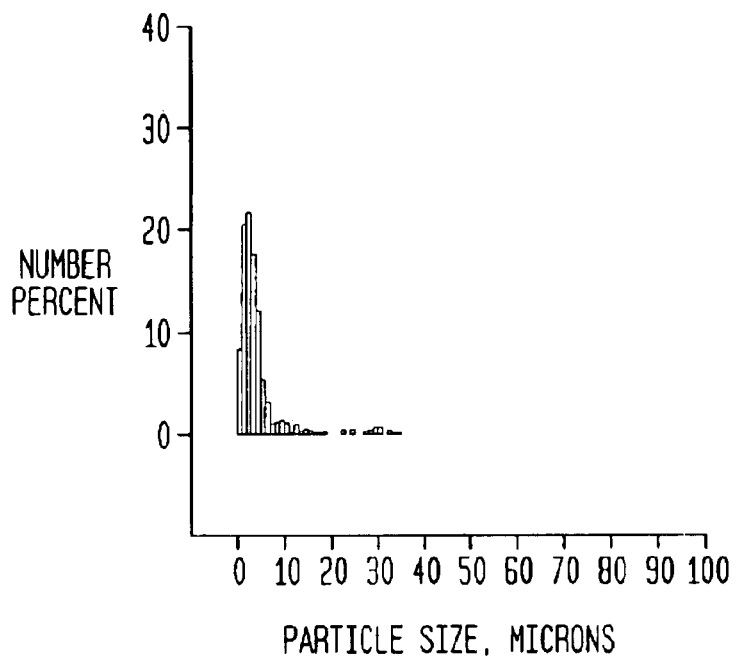
FIGS. 14a and 14b are particle size distribution of the "Third" sample of atomized aluminum powder.
Figure 14B:
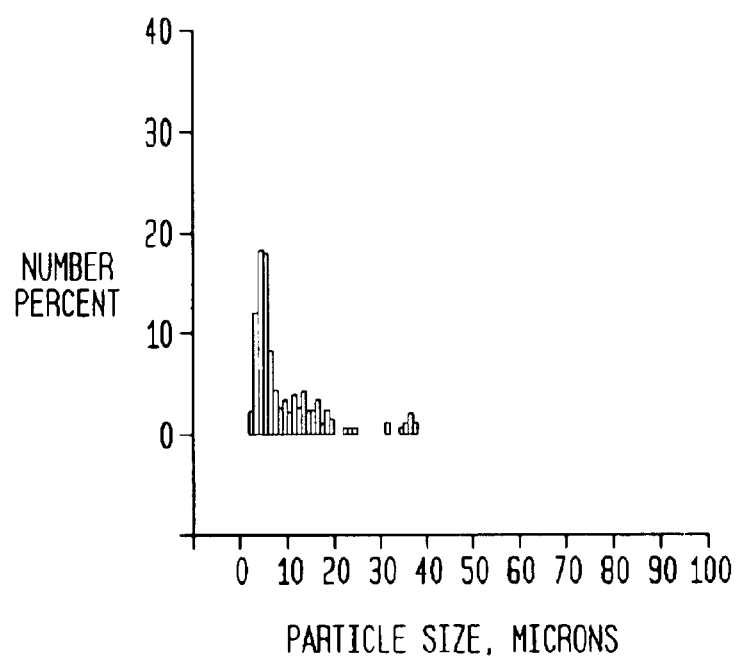
Figure 15A:
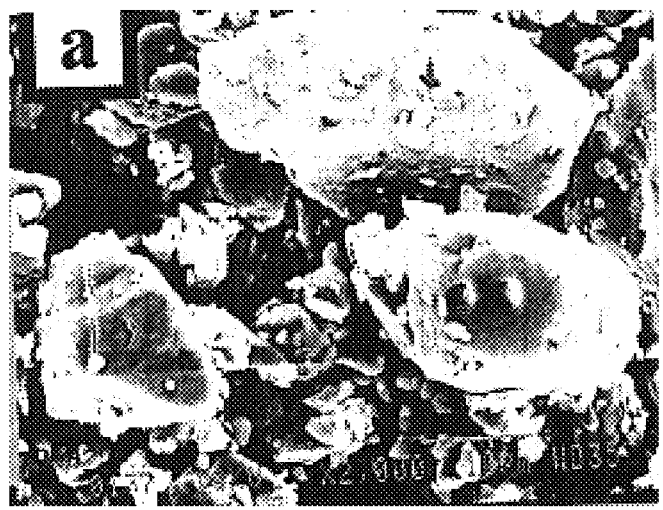
FIGS. 15a and 15b are SEM photomicrographs of HNIW powders.
Figure 15B:
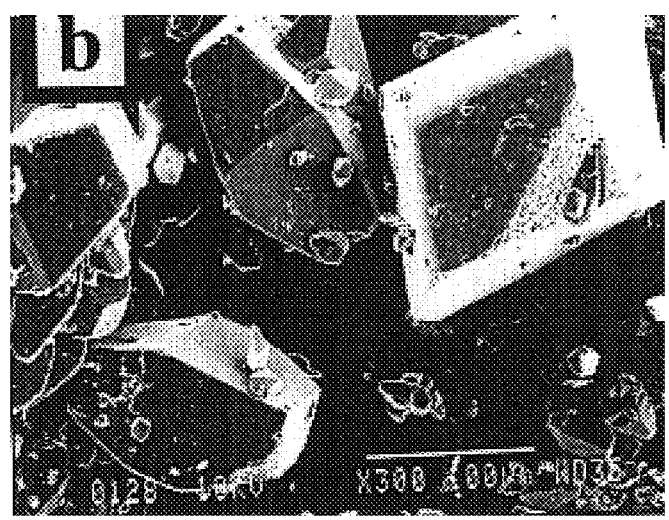

The technique has been also applied to other materials. The results of XAPS particle size distribution analysis of HNIW (hexanitro-hexaazaiso-wurtzitane) powders are shown in FIGS. 15a and 15b and 16. In these analysis "Fine" and "Course" HNIW powders were analyzed and similar calibration techniques, as with the aluminum powders, were applied to determine the particle size distributions. As shown in FIGS. 14a and 14b, particles as small as 0.5$\mu$ were present in the "Fine" HNIW powder, and in the "Coarse" HNIW powder particle size distribution approached a bimodal particle size distribution. These features were captured successfully with the XAPS analysis (see FIG. 16).

This demonstration is indicative of the ability of the technique of the present invention to capture changes in particle size distribution which can occur during crystallization, processing or heat treatment and suggests its potential for use as an off-line or on-line quality control monitoring technique during manufacturing operations.

Figure 3:
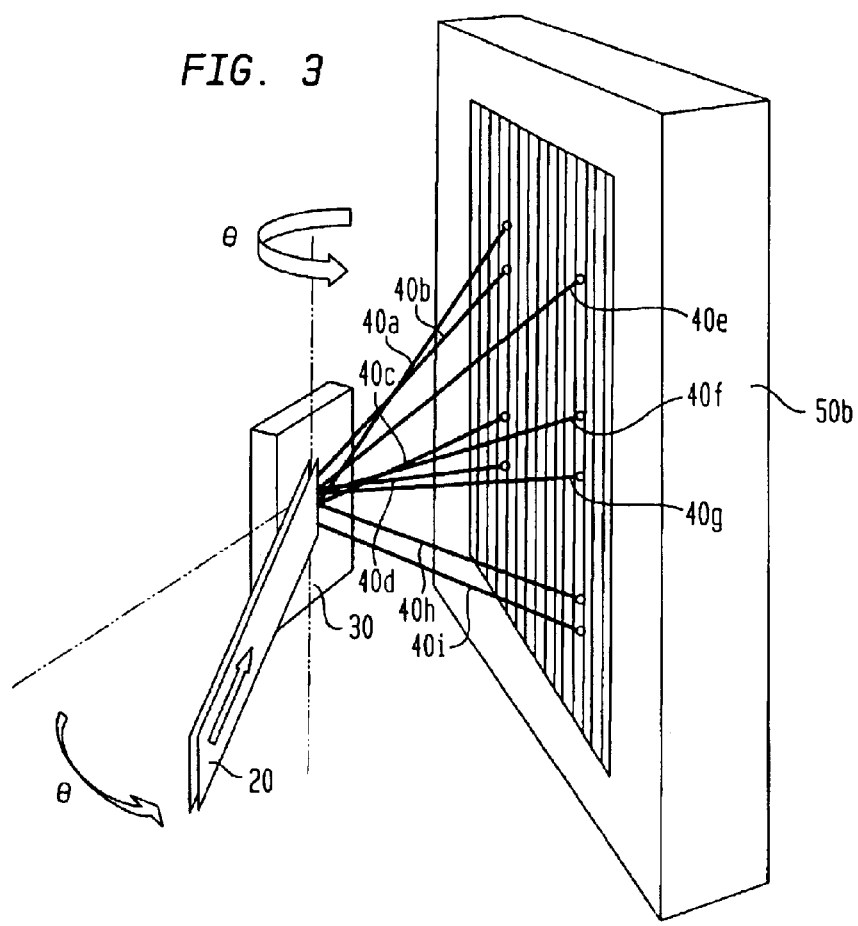
FIG. 3 is a schematic view of the present invention, X-ray Analyzer for Particle Size (XAPS), equipped with a position-sensitive area detector for simultaneous analysis of multiple Debye arcs from different lattice planes and multiple components/phases/polymorphs in a mixed composite material.

Every crystalline material generates characteristic diffraction peaks at different Bragg angles. In a multi-phase polymorph or composite material where two or more materials are mixed, particles from each material generate diffraction spots at separate Debye arcs positioned at unique θ angles. Particles with different crystal structures can be analyzed by the present invention by: (1) either sequentially placing a position sensitive linear detector (PSD) at the appropriate Debye arcs as shown in FIG. 1, or (2) simultaneously, by employing multiple linear PSD's, or a 2-dimensional PSD or a CCD camera, or a fiber-optic detector or an image plate or a film, or any other two-dimensional position sensitive detection system 50b, as shown in FIG. 3. By this technique of the present invention the particle size and relative particle volume fraction of multiple phases or polymorphs can be determined at a given location in the mixture, such as shown in FIG. 4, where 40a, 40b, 40c and 40d versus 40e, 40f, 40g, 40h and 40i could originate from two different phases or components.

Having thus described the invention in detail, it is to be understood that the foregoing description is not intended to limit the spirit and scope thereof. What is desired to be protected by Letters Patent is set forth in the appended claims.

What is claimed is:

1. A method of determining individual particle size and particle size distribution of particles in crystalline powders, suspensions and solids comprising the steps of:

generating an x-ray, narrowing the wavelength of said x-ray;

placing a specimen in the path of said narrowed wavelength x-ray, diffracting said narrowed wavelength x-ray with said specimen;

detecting said diffracted x-ray;

determining the position of the diffracted x-ray; and determining individual particle size and particle size distribution based on said position of said diffracted x-ray.

2. The method of claim 1 former comprising the step of rocking or rotating the specimen or the x-ray for successive times; and determining the position of the successive diffracted x-rays.

3. The method of claim 2 wherein said narrowing step employs a monochromator.

4. The method of claim 2 wherein said position of said diffracted x-ray detects the particles or grains in said specimen at their Bragg reflecting positions which have produced said diffracted x-ray along the appropriate Debye arc.

5. The method of claim 4 further including the step of determining the intensity distribution of said diffracted x-ray.

6. The method of claim 4 further including the steps of collecting intensity distributions of said diffracted x-ray for multiple particles and integrating the intensity of each diffracted x-ray to provide an indication of the volume and mass of a particular diffracting particle and determining the same for multiple particles to obtain the particle size distribution of the particle population in said specimen, and further, to differentiate the particles of mixed ingredients and determine their concentration in the mixture.

7. A method for determining individual particle size and particle size distribution of particles in crystalline powders, suspensions and solids comprising the steps of:

moving a sample into a testing position;

generating an x-ray from an x-ray source at a first position;

directing the x-ray at the testing position to impinge on the sample;

detecting diffracted x-rays;

moving the x-ray source to successive positions;

directing the x-ray at the testing position to successively impinge on the sample;

detecting diffracted x-rays; and determining individual particle size and particle size distribution based upon the detected diffracted x-rays.

8. The method of claim 7 wherein said position of said diffracted x-ray detects the particles or grains in said sample at their Bragg reflecting positions which have produced said diffracted x-ray along the appropriate Debye arc.

9. The method of claim 8 further including the step of determining the intensity dilution of said diffracted x-ray.

10. The method of claim 9 further including the steps of collecting intensity distributions of said diffracted x-ray for multiple particles and integrating the intensity of each diffracted x-ray to provide an indication of the volume and mass of a particular diffracting particle in said sample.

11. The method of claim 8 further comprising moving the x-ray source with the sample.

12. A method of determining particle size and particle size distribution of particles in crystalline powders, suspension and solids comprising the steps of:
collecting data on x-rays diffracted from specimens;
conditioning the collected data;
determining local maxima for the collected data;
separating peaks;
creating a three dimensional matrix of intensity versus azimuthal position versus rotational angle for the collected peak;
calculating integrated peak intensities; and
calculating particle size and particle size distribution.

13. An apparatus for determining individual particle size and particle size distribution of particles in crystalline powders, suspensions and solids corn comprising:
means for generating an x-ray;
means connected to said x-ray generating means for receiving said x-ray and for generating an x-ray output which has a narrower wavelength than said generated x-ray;
means for impinging said narrower wavelength x-ray on a specimen for producing a diffracted x-ray based on particle size and particle size distribution in said specimen;
detecting and position determining means connected to receive said diffracted x-ray for detecting said diffracted x-ray and for determining the position of said diffracted x-ray;
means connected to said specimen or said means for generating an x-ray for rocking or rotating said specimen or said x-ray generating means for successive impingements; and
means connected to said detecting and position determining means for measuring individual particle size and particle size distribution based on said position of said diffracted x-ray.

14. The apparatus of claim 13 wherein said means for generating a narrower wavelength x-ray includes a monochromator.

15. The apparatus of claim 13 wherein said detecting and position determining means detects particles or grains in said specimen at their Bragg reflecting positions which have produced said diffracted x-ray along the appropriate Debye arc.

16. The apparatus of claim 15 further including means connected to said detecting and position determining means for measuring the intensity distribution of said diffracted x-ray.

17. The apparatus of claim 16 further including means for collecting intensity distributions of said diffracted x-ray for multiple particles; and means connected to said intensity distribution collecting means for integrating the intensities of each diffracted x-ray for providing an indication of the volume and mass of a particular diffracting particle in said specimen.

18. An apparatus for analyzing individual particle size in a specimen, the apparatus comprising:
an x-ray source for generating an x-ray output signal;
monochromator means coupled to the x-ray source for producing a monochromatic parallel x-ray signal for irradiating a specimen and producing output signals indicative of particle characteristics of the specimen;
means for moving said specimen in the path of said monochromatic parallel x-ray signal;
position sensitive detector means for receiving said output signals from the specimen and generating output indications of the azimuthal and angular position of said output signals; and
computer means connected to receive said output indications for analyzing individual particle size and particle size distributions-of the specimen.

19. The apparatus of claim 18 wherein said position sensitive detector means detects particles or grains in said specimen at their Bragg reflecting positions which have produced said output signals along the appropriate Debye arc.

20. The apparatus of claim 19 further including means connected to said position sensitive detector means for measuring the intensity distribution of said output signals.

21. The apparatus of claim 20 further including means for collecting intensity distributions of said diffracted x-ray for multiple particles, and means connected to said intensity distribution collecting means for integrating the intensities of each diffracted x-ray for providing an indication of the volume and mass of a particular diffracting particle in said specimen.

22. An apparatus for analyzing individual particle size in a product during fabrication of the product, the apparatus comprising:
conveyor means for supporting and moving a product into position for measurement during fabrication;
x-ray generating means for irradiating said product for generating output radiation signals from said product;
means for moving said x-ray generating means in a predetermined pattern for successive intermittent irradiations;
position sensitive detector means for receiving said output radiation signals and for generating indications of the position sensitive detector means, said moving means and said conveyor means for analyzing said output radiation signals, controlling the position of said moving means and the operation of said conveyor means; and
means for determining individual particle size and particle size distributions.

23. The apparatus of claim 22 wherein said position of said output radiation signals detects the particles or grains in said products at their Bragg reflecting positions which have produced said diffracted x-ray along the appropriate Debye arc.

24. The apparatus of claim 23 further including means for determining the intensity distribution of said output radiation signals.

25. The apparatus of claim 24 further including means for collecting intensity distributions of said output radiation signals for multiple particles and integrating the intensity of each output radiation signal to provide an indication of the volume and mass of a particular diffracting particle.

26. The apparatus of claim 25, further comprising means for collecting and determining intensity distributions for multiple particles to obtain the particle size distribution of the particle population in said products, and further, to differentiate the particles of mixed ingredients and determine their concentration in the mixture.

* * * * *

UNITED STATES PATENT AND TRADEMARK OFFICE
CERTIFICATE OF CORRECTION

PATENT NO. : 6,751,287 B1
DATED : June 15, 2004
INVENTOR(S) : Dilhan M. Kalyon and Rahmi Yazici It is certified that error appears in the above-identified patent and that said Letters Patent is hereby corrected as shown below:

Column 1,
Line 18, delete the word "extractor" and replace with -- extract or --.

Column 4,
Line 7, delete the word "detennining" and replace with -- determining --.
Line 11, delete the word "extractor" and replace with -- extract or --.
Line 23, delete the word "polyrnorph" and replace with -- polymorph --.

Column 5,
Line 32, delete "K-α" and replace with -- Kα --.
Line 42, delete "500Xmagnification" and replace with -- 500X magnification --.

Column 6,
Line 53, delete "plasmadischarge" and replace with -- plasma discharge --.

Column 8,
Line 30, equation 1, referring to the first term in the parentheses, delete the character "l" and replace with the number -- 1 --.
Line 58, delete "CuKa" and replace with -- CuKα --.

Column 10,
Line 47, delete the word "nearspherical" and replace with -- near-spherical --.

Column 12,
Lines 13 and 16, delete the commas and replace with semicolons.
Line 25, delete the word "former" and replace with -- further --.

UNITED STATES PATENT AND TRADEMARK OFFICE
CERTIFICATE OF CORRECTION

PATENT NO. : 6,751,287 B1
DATED : June 15, 2004
INVENTOR(S) : Dilhan M. Kalyon and Rahmi Yazici It is certified that error appears in the above-identified patent and that said Letters Patent is hereby corrected as shown below:

Column 13,
Line 2, delete the word "dilution" and replace with -- distribution --.
Line 24, delete the word "corn".

Column 14,
Line 13, delete the hyphen after the word "distributions".

Signed and Sealed this

Twelfth Day of October, 2004

JON W. DUDAS
*Director of the United States Patent and Trademark Office*